(12) United States Patent
Redlingshöfer et al.

(10) Patent No.: US 7,790,934 B2
(45) Date of Patent: Sep. 7, 2010

(54) CATALYSTS AND PROCESS FOR DEHYDRATING GLYCEROL

(75) Inventors: Hubert Redlingshöfer, Münchsteinach (DE); Christoph Weckbecker, Gründau-Lieblos (DE); Klaus Huthmacher, Gelnhausen (DE); Andreas Dörflein, Großkrotzenburg (DE)

(73) Assignee: Evonik Degussa GmbH, Essen (DE)

( * ) Notice: Subject to any disclaimer, the term of this patent is extended or adjusted under 35 U.S.C. 154(b) by 0 days.

(21) Appl. No.: 12/687,909

(22) Filed: Jan. 15, 2010

(65) Prior Publication Data

US 2010/0113833 A1   May 6, 2010

Related U.S. Application Data

(62) Division of application No. 12/017,873, filed on Jan. 22, 2008, now abandoned.

(30) Foreign Application Priority Data

Jan. 29, 2007   (DE)   ........................ 10 2007 004 351

(51) Int. Cl.
    C07C 45/66   (2006.01)
    C07C 323/52  (2006.01)

(52) U.S. Cl. ........................... 568/486; 568/41

(58) Field of Classification Search ............... 568/486
    See application file for complete search history.

(56) References Cited

U.S. PATENT DOCUMENTS

| | | | |
|---|---|---|---|
| 4,508,918 A | 4/1985 | Yasuhara et al. | |
| 4,642,394 A * | 2/1987 | Che | 568/861 |
| 5,382,731 A | 1/1995 | Change et al. | |
| 5,387,720 A | 2/1995 | Neher | |
| 2006/0183945 A1 | 8/2006 | Redlingshofer et al. | |

FOREIGN PATENT DOCUMENTS

| | | |
|---|---|---|
| DE | 42 38 492 A2 | 11/1992 |
| DE | 42 38 493 C1 | 11/1992 |
| EP | 417 723 A2 | 9/1990 |
| EP | 0 598 229 A1 | 10/1993 |
| EP | 0 598 229 A | 5/1994 |
| EP | 1 402 947 A | 3/2004 |
| WO | 2006/087083 A | 8/2006 |
| WO | 2006/087083 A2 | 8/2006 |
| WO | 2006/087084 A2 | 8/2006 |

OTHER PUBLICATIONS

Tsukuda et al. "Production of Acrolein From Glycerol Over Silica-Supported Heteropoly Acids" Catalysis Communications, Elsevier Science, Amsterdam, NL—Bd. 8, Nr. 9; Dec. 12, 2006, Seiten 1349-1353.

Kurosaka et al., "Production of 1, 3-Propanediol by hydrogenolysis of glycerol catalyzed by Pt/W03/Zr02" Catalysis Communications, Elsevier Science, Amsterdam, NL, Bd. 9, Nr. 6; Dec. 4, 2007, Seiten 1360-1363.

Ullmann's Encyclopedia of Industrial Chemistry, 6th edition, 1999. Organic Synthesis I, 15-18 (1964).

Dao, Le H. et al., ACS symp. Ser.: 376 (Pyrolysis Oils Biomass) 328-341.

Studies in Surface Science and Catalysts, vol. 51, 1989: "New Solid Acids and Bases, Their Catalytic Properties" by K. Tanabe et al., Chapter 2, pp. 5-9; Chapter 1, pp. 1-3.

* cited by examiner

*Primary Examiner*—Sikarl A Witherspoon
(74) *Attorney, Agent, or Firm*—Smith, Gambrell & Russell, LLP

(57) ABSTRACT

A process for preparing acrolein from glycerol using an acidic solid-state catalyst which comprises tungsten compounds and further promoters.

22 Claims, No Drawings

CATALYSTS AND PROCESS FOR DEHYDRATING GLYCEROL

CROSS REFERENCE TO RELATED APPLICATIONS

This application is a division of U.S. patent application Ser. No. 12/017,873, filed 22 Jan. 2008, abandoned, and claims the benefit of DE 10-2007004351.3, filed 29 Jan. 2007, both of which are herein incorporated by reference in their entirety.

INTRODUCTION AND BACKGROUND

The invention relates to a process for preparing acrolein from glycerol using an acidic catalyst which comprises tungsten compounds and at least one further promoter.

Acrolein is an important intermediate and is of great economic significance for the preparation of acrylic acid, D,L-methionine and the methionine hydroxy analogue 2-hydroxy-4-methylthiobutyric acid (MHA). Methionine is an essential amino acid which is used, inter alia, as a supplement in feeds. Nutrition-improving feed additives are nowadays an indispensable constituent in animal nutrition. They serve for better utilization of the food supply, stimulate growth and promote protein formation. One of the most important of these additives is the essential amino acid methionine, which assumes a prominent position as a feed additive in poultry breeding in particular. In this field, though, methionine replacements such as methionine hydroxy analogue (abbreviated to MHA) also have not inconsiderable significance, since they have similar growth-stimulating properties to the amino acid known for this purpose. Acrylic acid is an important starting material for preparing polymers which, for example owing to their water absorption capacity, are used as superabsorbents.

According to the prior art, acrolein is synthesized by heterogeneously catalysed selective oxidation of propene over mixed oxide catalysts. EP 417723 describes the synthesis over complex mixed multimetal oxide catalysts at temperatures of 300 to 380° C. and pressures of 1.4 to 2.2 bar. Ullmann's Encyclopedia of Industrial Chemistry, 6th edition, 1999 describes the overall process including workup, in which several by-products are removed. Once the reactant mixture of propene, air and water has been converted at least partly over the catalyst, quenching is first effected to remove high-boiling by-products such as polymers, acrylic acid and acetic acid. In the downstream absorber, acrolein is washed out. After the desorption, the absorbent is recovered by purifying the crude acrolein obtained by distillation in several stages.

It is known that glycerol can be dehydrated in the presence of acidic substances to various products. According to Organic Synthesis I, 15-18 (1964), treatment of a mixture of pulverulent potassium hydrogensulphate, potassium sulphate and glycerol at 190 to 200° C. affords acrolein in a yield of between 33 and 48%. Owing to the low yields and the high salt burdens, this process is, however, not suitable for the industrial scale.

In the course of studies of model substances of biomass pyrolysis oils, the catalytic treatment of glycerol over H-ZSM5 zeolites at 350 to 500° C. has also been studied—see Dao, Le H. et al. ACS Symp. Ser.: 376 (Pyrolysis Oils Biomass) 328-341 (1988). Hydrocarbons are formed only in low yields.

Moreover, EP 0598229, U.S. Pat. No. 5,387,720 describe the acid-catalysed conversion of glycerol to acrolein in the gas phase and in the liquid phase. In this case, it is solely the acid strength (Hammett acid function) that determines suitability as a catalyst. DE 42 38 492 relates to the synthesis of 1,2- and 1,3-propanediol by dehydrating glycerol with high yields.

WO 2006/087083 discloses a process for preparing acrolein from glycerol over acidic catalysts, in which oxygen is added to the reaction mixture.

A similar process is described in WO 2006/087084. The catalysts used there have a Hammett acidity $H_o$ in the range of −9 to −18.

SUMMARY OF THE INVENTION

It is an object of the invention to provide a catalyst for the dehydration of glycerol, which has a relatively low carbonization tendency and is easy to regenerate.

The invention provides solid-state catalysts which comprise tungsten compounds and have a Hammett acidity $H_o$ of <+2 and which comprise one or more promoters selected from compounds of the group of elements comprising, especially consisting of, gold, silver, copper, platinum, rhodium, palladium, ruthenium, samarium, cerium, yttrium, scandium, lanthanum, zinc, magnesium, iron, cobalt or nickel or mixtures thereof. Suitable promoters are also, in particular, acidic zeolites or montmorillonite, which are then present optionally in each case in an amount of 0.1 to 30% by weight, in particular 5 to 25% by weight, based on the catalyst, in addition to the abovementioned promoters or alone.

Depending on their standard potential, individual elements among those mentioned above may also be present in metallic form on the catalyst.

Preference is given to catalysts which have a Hammett acidity $H_o$ of <+2 to −20.

Likewise provided in accordance with the invention is a process for preparing acrolein from glycerol, in which these catalysts are used.

DETAILED DESCRIPTION OF INVENTION

It has been found that the presence of Brønsted-acidic sites on the catalyst surface is not sufficient to achieve good yields of acrolein. In addition, it has been found that the presence of tungsten compounds and the combination thereof with acidic sites improves the yields.

Since glycerol is a reactive molecule which tends to form relatively high-boiling compounds at high temperatures by the reaction of two or more glycerol molecules with one another, the catalyst is carbonized by deposits of carbon-containing molecules on the surface. This leads to a reduction in activity.

To achieve a high space-time yield, it is not only the Hammett acid strength of the catalyst that is important, but also the regenerability and the tendency to carbonization.

The inventive catalyst comprises one or more promoters which accelerate(s) the regeneration of the catalyst. In addition, lifetime and space-time yield increase significantly, since deactivation by carbonization in particular is at least for the most part eliminated in the case of these catalysts, and the activity is significantly increased. The conversion of glycerol and the yield of acrolein can thus be maintained at a high level depending on the time. This is of great significance especially for an industrial implementation of the synthesis, since an exchange of the catalyst and associated plant shutdowns cause high costs.

In addition to the Brønsted-acidic groups, it is also possible for hydroxyl groups or Lewis-acidic sites to influence the activity and selectivity. Equally, irrespective of the promoters, the addition of compounds of one or more of the elements selected from the group comprising silicon, phosphorus, niobium, zinc, tin, magnesium, aluminium or molybdenum to a catalyst comprising tungsten compounds can modify the surface of the catalyst or reduce the concentration of active sites, such that the selectivity is improved further. This especially reduces the formation of high boilers or coke precursors which are formed from two or more adjacent adsorbed glycerol molecules or intermediates and are adsorbed in a fixed manner.

These compounds thus serve to lower the concentration of the active sites on the catalyst surface and thus to increase the distance between adjacent active sites (site isolation). This in turn reduces the probability that two glycerol molecules or reactive intermediates or coke precursors which have been formed react with one another on the surface to give higher hydrocarbons.

Suitable solid-state catalysts are especially also the types known from U.S. Pat. No. 5,387,720 (EP 0 598 229 A1), when they additionally comprise a tungsten compound and one or more of the promoters mentioned. These catalysts are solid substances which are essentially insoluble in the reaction medium, have a mono- or polyphasic structure and have an $H_o$ of less than +2, preferably less than −3. The $H_o$ corresponds to the Hammett acid function and can be determined by the so-called amine titration using indicators or by adsorption of a gaseous base—see Studies in Surface Science and Catalysis, Vol. 51, 1989: "New solid acids and bases, their catalytic properties" by K. Tanabe et al. chapter 2, especially pages 5-9. Chapter 1 (pages 1-3) of the aforementioned document mentions numerous solid acids from which the person skilled in the art, if appropriate after determining the $H_o$ value, can select the suitable catalyst for the inventive modification. Suitable base substances for the inventive dehydration catalysts are preferably (i) natural and synthetic silicatic substances, especially mordenite, acidic zeolites and activated carbon; (ii) support materials, such as oxidic or silicatic substances, for example $Al_2O_3$, $SiO_2$, $ZrO_2$, $TiO_2$; $Nb_2O_5$, modified with mono-, di- or polybasic inorganic acids or acid salts of inorganic acids; (iii) oxides and mixed oxides, for example $\gamma$-$Al_2O_3$ and ZnO—$Al_2O_3$, $SiO_2$—$Al_2O_3$, $ZrO_2$—$SiO_2$, $ZrO_2$—$HfO_2$ mixed oxides or heteropolyacids.

Suitable compounds for providing the active tungsten sites may, for example, be ammonium tungstate, ammonium metatungstate, tungstic acid, tungstosilicic acid, tungstophosphoric acid, tungsten oxides or heteropolyacids with tungsten as a constituent. These compounds or mixtures thereof are then either used directly as the catalyst or used as catalyst precursors. In the case of addition of further elements, preference is given to a preceding mixing as a powder, in a solution or in a melt. In one embodiment of the invention, the catalytically active compounds are bound on a support.

The support materials used may, for example, be aluminum oxide, titanium dioxide, silicon dioxide, zirconium dioxide, activated carbon or mixtures thereof. The supports serve predominantly to increase the specific surface area or to fix the active sites.

The inventive catalysts are prepared by processes known to those skilled in the art. When the active components are applied to a support, this is preferably done by impregnating the support, for example by means of the incipient-wetness method by spraying. The active components may also be obtained by precipitation or extraction from a solution. Subsequently, the catalyst can then be shaped, if appropriate with addition of supports, adhesion promoters or pore formers, by pressing, extrusion, coating or agglomeration. The catalyst typically has a particle diameter between 0.04 mm and 20 mm, preferably between 0.1 and 10 mm, especially between 0.5 and 7 mm. The active compounds may also be applied in the form of a coating. When no support is used, preference is given to catalyst preparation by extrusion, pressing of tablets or buildup by agglomeration.

For the dehydration in the gas phase, particular preference is given to catalysts having an $H_o$ between −3 and −8.2. Suitable catalyst systems which comprise tungsten compounds and promoters are, for example, $Pd/H_2WO_4$, $Pt/H_2WO_4$, $Pd/WO_x/ZrO_2$, $Cu/WO_x/ZrO_2$. The invention likewise provides a process for preparing acrolein by dehydrating glycerol in the presence of solid-state catalysts which comprise tungsten compounds and have a Hammett acidity $H_o$ of <+2 to preferably −20 and which comprise one or more promoters selected from compounds of the group of elements comprising, preferably consisting of, gold, silver, copper, platinum, palladium, rhodium, ruthenium, samarium, cerium, yttrium, scandium, lanthanum, zinc, magnesium, iron, cobalt or nickel, or mixtures thereof and optionally additionally comprising compounds from the group of elements lithium, sodium, potassium or caesium and/or montmorillonite or acidic zeolites, these compounds being present optionally in an amount of 0.1 to 30% by weight, especially 5 to 25% by weight, based on the catalyst.

The dehydration is effected preferably in the absence of oxygen. In one embodiment, also in the presence of hydrogen in an amount of 0.1 to 10% by volume, in particular of 0.5 to 5%, based on the total amount of the reaction mixture. The dehydration is performed in the presence of the catalysts described above.

The concentration of the glycerol in the reaction mixture is preferably lowered by the addition of suitable gaseous compounds inert under the selected reaction conditions.

As a result, side reactions to give oligomers, polymers and other high boilers are minimized. The solvents and diluents known to those skilled in the art are used, for example water, nitrogen, air, carbon dioxide, methane and/or hydrogen, alcohols, for example methanol and ethanol, acetone, toluene or methyl isobutyl ketone. Preference is given to dilution media which, after the condensation, can be isolated from acrolein in a simple manner by phase separation.

In the reaction mixture, the glycerol concentration is between 1 and 100% by weight, preferably between 1 and 70% by weight and especially between 5 and 40% by weight.

One advantage of the process consists in the fact that glycerol solutions having a content of 5 to 40% by weight are also usable. So-called crude glycerols without preceding concentration or purification can thus be used directly for the synthesis of acrolein.

The reaction is performed at a temperature between 150 and 450° C., preferably between 180 and 350° C., more preferably between 220 and 320° C. Typically, the pressure is between 0.1 and 200 bar, preferably between 0.5 and 50 bar, more preferably between 0.9 and 10 bar.

The process can be performed in the liquid phase or in the gas phase. In both embodiments, the same acidic solid-state catalysts can be used in principle, but it has been found that particular catalysts are preferably suitable for dehydration in the gas phase and others preferably for that in the liquid phase.

The reaction in the gas phase is particularly preferred because the glycerol conversion is virtually complete (>95%) and the gaseous reaction mixture leaving the catalyst can be condensed or absorbed directly to obtain an aqueous acrolein solution which additionally comprises by-products which have been formed; this condensate can in many cases be processed further directly. The partial condensation and/or absorption of the reaction mixture can be effected in several stages. If desired, acrolein can be obtained from the reaction mixture, if appropriate together with a portion of the water, by fractional condensation, absorption, desorption and subsequent distillation.

A portion of the water is circulated, in the course of which it is evaporated and condensed with utilization of thermal integration. An inert gas or a diluent can also be circulated.

Acrolein formed is removed from the reaction mixture alone or together with a portion of the water and small amounts of by-products in a known manner, typically by distillation, by absorption or by $N_2$ stripping. The acrolein can be isolated by condensation or scrubbing with water. The glycerol-containing reaction mixture freed of acrolein is recycled into the dehydration stage. One advantage of dehydration in the liquid phase over that in the gas phase consists in the lower energy demand, because only the acrolein removed from the reaction mixture and a portion of water which is distilled over with it have to be evaporated.

The dehydration in the gas phase is effected preferably within the temperature range between 240 and 320° C., that in the liquid phase preferably between 200 and 300° C. In the case of liquid phase dehydration, the apparatus is subjected to at least such a pressure which is sufficient to maintain the liquid phase.

The dehydration is effected in a fixed bed reactor, a fluidized bed reactor, in a reactor with a circulating fluidized bed, a moving bed reactor or a reactor with regenerator-riser (-downer) design. It can be performed continuously or batchwise.

Moreover, the combination of the reaction with reactant workup or product workup by means of a reactive distillation is possible and advisable, since the boiling point differences between glycerol and acrolein are very large. In this case, the catalyst is positioned either in the bottom and/or in the column part. The catalyst introduced may, for example, be present in the form of a bed, suspension or a coating. A further advantage of the reactive distillation consists in the fact that high-boiling impurities are discharged from crude glycerol at the bottom of the column with further high boilers which can be formed as by-products. Acrolein and low boilers are then removed via the top.

Acrolein formed can also be removed from the reaction mixture in a known manner, alone or together with a portion of the solution or dilution medium, by stripping, distillation or extraction. Unconverted glycerol can then be recycled into the reaction stage.

The invention also provides a process, especially for preparing methylmercaptopropionaldehyde (MMP) from glycerol, without isolating intermediates, in which the multistage synthesis of MMP according to the prior art can now be performed in one stage using the inventive catalyst.

The process relates to the preparation of compounds of the general formula

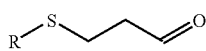 (I)

in which

R: H, $C_1$ to $C_3$-alkyl, by the reaction with glycerol, or with a compound from which glycerol is formed, with a compound of the general formula

 (II)

in which

R: H, $C_1$ to $C_3$-alkyl in the presence of the inventive catalyst.

The preferred product is MMP, which is prepared using methyl mercaptan.

In this case, for example, a glycerol-methyl mercaptan mixture, optionally in the presence of a solvent, is converted over an inventive solid-state catalyst either in the liquid phase or in the gas phase.

When the synthesis is effected in the liquid phase, a reaction temperature between 50 and 500° C., preferably between 80 and 350° C., more preferably between 120 and 300° C. is employed. The pressure is adjusted such that the liquid state of the reaction mixture is maintained. Typically, the pressure is between 1 and 300 bar, preferably between 5 and 200 bar, more preferably between 20 and 150 bar.

The inventive catalyst also features good regenerability and slow deactivation/carbonization.

The regeneration can be effected either under oxidation conditions or under hydrogenation conditions. In both cases, the coke which has formed on the surface of the catalyst by deposition of hydrocarbons during the reaction is removed completely or partly. The suitable promoters which are part of the catalyst are, in the case of regeneration by oxidation, generally components which accelerate the conversion of hydrocarbons to carbon oxides, for example compounds which comprise gold, silver, copper, cerium, iron or platinum, individually or in a mixture, optionally these elements in metallic form. When the regeneration is performed under hydrogenating conditions, the acidic catalyst preferably comprises promoters with strongly hydrogenating action, for example compounds of the elements cobalt, nickel, palladium, platinum, ruthenium or rhodium, individually or in a mixture, if appropriate also in elemental form. Also possible is a combination of several effects by addition of one or more promoters.

The regeneration is effected separately from the conversion of glycerol, either in time or in location. In the case of time separation, the feeding of glycerol into this reactor is stopped and then the regeneration is performed before the reactant mixture is fed in again. This operation is then repeated periodically as often as desired. For the performance of this regeneration method, suitable arrangements are especially the cyclic operation of 2 or more fixed bed reactors in order to be able to obtain a continuous product stream. In this case, one of the reactors is regenerated while at least one of the reactors is used for the production of acrolein. The time intervals for reaction and regeneration can be selected as desired. Preference is given to the uninterrupted production of acrolein within a time interval of 2 to 3000 h, especially 4 to 400 h, before the catalyst is regenerated within a time interval of 0.5 to 100 h, especially 1 to 10 h.

When the regeneration is effected at a separate location, the catalyst is moved continuously between preferably 2 reactors. In one of the reactors, the glycerol conversion to acrolein takes place continuously. In the other reactor, the catalyst is regenerated continuously. Suitable reactor designs are the moving bed reactor or the regenerator-riser (-downer) design. The moving bed is notable for relatively low throughput of the catalyst and less catalyst abrasion and is preferred here.

Between the regeneration and the reaction, it is in each case advisable to perform a flush step, preferably with nitrogen. In the case of regeneration, higher temperatures of 100 to 800° C., preferably 200 to 700° C., especially 300 to 550° C., are employed. These need not correspond to the reactor temperature during the glycerol conversion. In that case, corresponding heating and cooling steps are required. For the regeneration of the catalyst, preference is given to employing a higher temperature than in the reaction. The pressure in the regeneration is preferably between 0 and 50 bar, especially between 0 and 3 bar.

To regenerate the catalyst, at least one additive is used. This is preferably gaseous. When regeneration is effected under oxidizing conditions, it is a gaseous oxidizing agent. Preference is given to using air or oxygen or carbon dioxide. When regeneration is effected by hydrogenation, it is a gaseous reducing agent. In that case, preference is given to using hydrogen. To avoid high excess temperatures in the catalyst zone as a result of the exothermic removal of the coke, the reducing gas is preferably used in diluted form, for which, for example, nitrogen or steam is used. During the regeneration of the catalyst, the concentration of the additive is preferably increased stepwise. The catalyst may be diluted by solid inert material or else be arranged in different zones.

The desired catalytic properties and/or the acid function of the catalyst does not disappear in the course of regeneration of the inventive catalysts, as observed, for example, in the case of the catalysts prepared from classical acids, such as phosphoric acid or hydrochloric acid, and leads to catalyst deactivation.

EXAMPLES

Comparative Example 1

A catalyst according to German Patent Specification DE 4238493 which is incorporated herein by reference was used: 100 g of silicon oxide support having a diameter of about 4 mm were mixed with 25 g of 20% by weight phosphoric acid for 1 h. On a rotary evaporator, the excess water was then removed at approx. 70° C. 18 ml of this catalyst were introduced into a fixed bed reactor with a diameter of 15 mm. The reaction was then heated to a temperature of 250° C. By means of a pump, 12.5 g/h of a 20% by weight aqueous glycerol solution were passed into the reactor through an evaporator heated to 260° C. By means of gas chromatography, the stream was analysed at the reactor outlet. Up to an operating time of about 15 h, full conversion of glycerol could be observed. The selectivity and thus the yield were 79%. After approx. 15 h, the conversion and hence the yield fell steeply, such that only a conversion of 20% was present after 23 h. After the catalyst had been flowed through exclusively by a hydrogen stream of 4 l (STP)/h at a temperature of 350° C. for 5 h, no improvement in the yield (regeneration) could be detected. After the catalyst had been flowed through exclusively with an air stream of 4 l (STP)/h at a temperature of 350° C. for 5 h, a further deterioration in the yield was even detected.

Comparative Example 2

Comparative Example 1 was repeated, except that molybdic acid pressed to tablets was used as the catalyst. At a reactor temperature of 250° C., a yield of 9% was achieved within the first 5 h. Regeneration was dispensed with.

Example 1

Comparative Example 1 was repeated, except that tungstic acid pressed to tablets was used as the catalyst. At a reactor temperature of 260° C., a full conversion and a yield of 79% were achieved within the first 5 h. Within the next operating hours, the conversion and, correspondingly, the yield were reduced significantly. In the further course, a decline in the yield by approx. 5% per 10 h was detected. After the catalyst had been flowed through exclusively with a hydrogen stream of 4 l (STP)/h at a temperature of 350° C. for 10 h, the activity of the catalyst was improved significantly. The glycerol conversion was again complete at the start. In the further course, the conversion and the yield were reduced as before the regeneration. This cyclic operation of glycerol dehydration and regeneration of the catalyst was repeated three times within 300 h. After the unregenerated catalyst had been deinstalled, it was black in colour. The carbon content of the catalyst was 22% by weight, which indicates considerable carbonization.

Example 2

Comparative Example 1 was repeated, except that tungstic acid pressed to tablets was used as the catalyst. This catalyst was additionally impregnated with 1% by weight of Pd. To this end, lead acetate was used by means of incipient wetness. At a reactor temperature of 260° C., a full conversion and a yield of 77% were achieved within the first 5 h. Within the next operating hours, the conversion and, correspondingly, the yield were reduced significantly. After the catalyst had been flowed through exclusively with a hydrogen stream of 4 l (STP)/h at a temperature of 350° C. for 10 h, the activity of the catalyst was improved significantly. The glycerol conversion was then complete again at the start. Compared to Example 1, the decline in the conversion in the dehydration reaction was significantly lower after the regeneration, and the high conversion level was maintained for longer.

Example 3

Comparative Example 1 was repeated, except that a powder mixture of 15% by weight of montmorillonite and 85% by weight of $WO_3/ZrO_2$ (11% by weight of $WO_3$ on $ZrO_2$) pressed to tablets was used as the catalyst. At a reactor temperature of 260° C., a full conversion and a yield of 79% were achieved within the first 5 h. Within the next operating hours, the conversion and, correspondingly, the yield were reduced. After the catalyst had been flowed through exclusively with an air stream of 4 l (STP)/h at a temperature of 300° C. for 5 h, the activity of the catalyst was improved significantly. During the first hour of the regeneration, the air was diluted 1:1 with nitrogen in order to limit the exothermicity as a result of the burning-off of the coke. The glycerol conversion was again complete at the start after the regeneration. After 6 cycles of dehydration and of regeneration had been passed through, the regeneration temperature was increased to 390° C. In the subsequent dehydration, this led to a significantly enhanced conversion profile, where the glycerol conversion was still more than 90% after approx. 20 h. Further variations and modifications of the foregoing invention will be apparent to those skilled in the art and are intended to be encompassed by the claims appended hereto.

The invention claimed is:

1. A process for preparing acrolein by dehydrating glycerol in the presence of a solid-state catalyst which comprises at least one tungsten compound selected from the group consisting of ammonium tungstate, tungstic acid, and tungsten oxides and has a Hammett acidity $H_o$ of <+2 and which includes at least one promoter compound selected from the group consisting of components of gold, silver, copper, vanadium, platinum, rhodium, palladium, ruthenium, samarium, cerium, yttrium, scandium, lanthanum, zinc, magnesium, cobalt, nickel and mixtures thereof, and optionally a compound of an element selected from the group consisting of lithium, sodium, potassium or cesium, and mixtures thereof, and/or montmorillonite or an acidic zeolite.

2. The process according to claim 1, in which the solid-state catalyst contains montmorillonite or acidic zeolites in an amount of 0.1 to 30% by weight.

3. The process according to claim 1, in which the dehydrating is effected in the absence of oxygen.

4. The process according to claim 1, in which the dehydrating is effected in the presence of hydrogen.

5. The process according to claim 1, in which glycerol is used in an amount of 1 to 100% based on the total amount of the reaction mixture, containing glycerol, any remaining amount up to 100% consisting of compounds inert under reaction conditions.

6. The process according to claim 1, in which an inert compound is used which is nitrogen and/or water.

7. The process according to claim 1, in which pressures between 1 and 300 bar and temperatures between 150 and 450° C. are employed.

8. The process according to claim 1, which is carried out at pressures between 1 and 100 bar and at temperatures between 180 and 350° C.

9. The process according to claim 1, carried out in the gas phase.

10. The process according to claim 1, in which dehydrating is performed in a fixed bed reactor, in a fluidized bed reactor, in a reactor with a circulating fluidized bed, in a moving bed reactor or in a reactor with regenerator-riser (-downer) design.

11. The process according to claim 1, which produces a reaction mixture which is worked up with utilization of partial condensation, absorption, desorption and/or distillation.

12. The process according to claim 1, in which a portion of water is circulated and is evaporated and condensed with utilization of thermal integration.

13. The process according to claim 1, in which an inert gas or diluent is circulated.

14. The process according to claim 1, in which unconverted glycerol is sent to an incineration or a distillation for crude glycerol.

15. The process according to claim 1, in which the glycerol used has been obtained from hydrolysis of fats.

16. The process according to claim 1, in which the glycerol used has been obtained from generation of fuels from natural raw materials.

17. The process according to claim 1, in which the catalyst, after dehydrating, is regenerated under oxidizing conditions.

18. The process according to claim 1, in which the catalyst, after dehydrating, is regenerated under reducing conditions.

19. The process according to claim 17, in which a catalyst which comprises one promoter compound selected from the group consisting of compounds of gold, silver, copper, cerium, iron, platinum, and mixtures thereof is used.

20. The process according to claim 18, in which a catalyst is used which comprises a promoter compound selected from the group consisting of compounds of cobalt, nickel, palladium, platinum, ruthenium, rhodium, and mixtures thereof.

21. A process for preparing a compound of the formula

(I)

in which

R is H, or $C_1$ to $C_3$-alkyl, comprising reacting glycerol with a compound of the formula

(II)

in which

R is H or $C_1$ to $C_3$-alkyl in the presence of a solid-state catalyst which comprises at least one tungsten compound selected from the group consisting of ammonium tungstate, tungstic acid, and tungsten oxides and has a Hammett acidity $H_o$ of <+2 and which includes at least one promoter compound selected from the group consisting of components of gold, silver, copper, vanadium, platinum, rhodium, palladium, ruthenium, samarium, cerium, yttrium, scandium, lanthanum, zinc, magnesium, cobalt, nickel and mixtures thereof, and optionally a compound of an element selected from the group consisting of lithium, sodium, potassium or cesium, and mixtures thereof, and/or montmorillonite or an acidic zeolite.

22. A process for preparing acrolein which comprises dehydrating glycerol in the presence of a solid-state catalyst having at least one tungsten compound selected from the group consisting of ammonium tungstate, tungstic acid, and tungsten oxides and a Hammett acidity $H_o$ of <+2, regenerating the solid-state catalyst and dehydrating additional glycerol in the presence of the regenerated solid-state catalyst, and lowering the decline in conversion by the regenerated solid-state catalyst by including at least one promoter compound selected from the group consisting of components of gold, silver, copper, vanadium, platinum, rhodium, palladium, ruthenium, samarium, cerium, yttrium, scandium, lanthanum, zinc, magnesium, cobalt, nickel and mixtures thereof, and optionally a compound of an element selected from the group consisting of lithium, sodium, potassium or cesium, and mixtures thereof, and/or montmorillonite or an acidic zeolite in the solid-state catalyst prior to use.

\* \* \* \* \*